United States Patent [19]

Goldenring et al.

[11] Patent Number: 6,107,048
[45] Date of Patent: Aug. 22, 2000

[54] METHOD OF DETECTING AND GRADING DYSPLASIA IN EPITHELIAL TISSUE

[75] Inventors: James R. Goldenring, Martinez; Gregory S. Ray, Snellville; Jeffrey R. Lee, Martinez, all of Ga.

[73] Assignee: Medical College of Georgia Research Institute, Inc., Augusta, Ga.

[21] Appl. No.: 08/974,692

[22] Filed: Nov. 20, 1997

[51] Int. Cl.⁷ .......................... G01N 33/53; C07K 16/00; C12Q 1/68
[52] U.S. Cl. .................... 435/7.1; 530/387.1; 530/387.7; 435/6
[58] Field of Search .................................. 435/6, 29, 34, 435/7.1, 810; 436/64, 172, 164, 63; 530/387.1, 387.7, 388.1, 388.15

[56] References Cited

PUBLICATIONS

Hollstein, M. et al, p53 Mutations in Human Cancers, Science 253, pp. 49–52, Jul. 5, 1991.

Ahle, et al., "Structural relationships between clathrin assembly proteins from the Golgi and the plasma membrane," *EMBO J.* 7(4):919–929 (1988).

Blount, et al., "17p Allelic Deletions and p53 Protein Overexpression in Barrett's Adenocarcinoma," *Cancer Res.* 51(20):5482–5486 (1991).

Blount, et al., "17p Allelic Losses in Diploid Cells of Patients with Barrett's Esophagus Who Develop Aneuploidy," *Cancer Res.* 54(9):2292–2295 (1994).

Calhoun, et al., "Rab Proteins in Gastric Parietal Cells: Evidence for the Membrane Recycling Hypothesis," *Yale J. Bio. Med.* 69(1):1–8 (1996).

Calhoun, et al., "Two Rab proteins, vesicle–associated membrane protein 2 (VAMP–2) and secretory carrier membrane proteins (SCAMPs), are present on immunoisolated parietal cell tubulovesicles," *Biochem. J.* 325(2):559–564 (1997).

Casson, et al., "Clinical Implications of p53 Gene Mutation in the Progression of Barrett's Epithelium to Invasive Esophageal Cancer," *Am. J. Surg.* 167(1):52–57 (1994).

Goldenring, et al., "Identification of a Small GTP–binding Protein, Rab25, Expressed in the Gastrointestinal Mucosa, Kidney, and Lung," *J. Biol. Chem.* 268(25):18419–18422 (1993).

Goldenring, et al., "Enrichment of rab11, a small GTP–binding protein, in gastric parietal cells," *Am. J. Physiol.* 267(2):G187–G194 (1994).

Goldenring, et al., "Rab11 is an apically located small GTP–binding protein in epithelial tissues," *Am. J. Physiol.* 270(3):G515–G525 (1996).

Gray, et al., "Epithelial Proliferation in Barrett's Esophagus by Proliferating Cell Nuclear Antigen Immunolocalization," *Gastroenterology* 103(6):1769–1776 (1992).

Haggitt, "Barrett's Esophagus, Dysplasia, and Adenocarcinoma," *Hum. Pathol.* 25(10):982–993 (1994).

Hameeteman, et al., "Barrett's Esophagus: Development of Dysplasia and Adenocarcinoma," *Gastroenterology* 96(5):1249–1256 (1989).

Hardwick, et al., "Adenocarcinoma arising in Barrett's oesophagus: evidence for the participation of p53 dysfunction in the dysplasia/carcinoma sequence," *Gut* 35:764–768 (1994).

Iftikhar, et al., "Length of Barrett's oesophagus: an important factor in the development of dysplasia and adenocarcinoma," *Gut* 33:1155–1158 (1992).

Isolauri, et al., "Prevalence of Symptoms Suggestive of Gastro–oesophageal Reflux Disease in an Adult Population," *Ann. Med.* 27(1):67–70 (1995).

Jones, et al., "Potential Application of p53 as an Intermediate Biomarker in Barrett's Esophagus," *Ann. Thorac. Surg.* 57(3):598–603 (1994).

Klumperman, et al., "Differences in the Endosomal Distributions of the Two Mannose 6–Phosphate Receptors," *J. Cell. Biol.* 121(5):997–1010 (1993).

Levine, et al., "Correlation of Ultrastructural Aberrations With Dysplasia and Flow Cytometric Abnormalities in Barrett's Epithelium," *Gastroenterology* 96(2):355–367 (1989).

Levine, et al., "Specialized Metaplastic Columnar Epithelium in Barrett's Esophagus—A Comparative Transmission Electron Mciroscopic Study," *Lab Invest.* 60(3):418–431 (1989).

Levine, et al., "An Endoscopic Biopsy Protocol Can Differentiate High–Grade Dysplasia From Early Adenocarcinoma in Barrett's Esophagus," *Gastroenterology* 105(1):40–50 (1993).

Lindner, et al., "Clathrin–associated Proteins of Bovine Brain Coated Vesicles," *J. Biol. Chem.* 267(23):16567–16573 (1992).

Lindner, et al., "Light–Chain–Independent Binding of Adaptors, AP180, and Auxillin to Clathrin," *Biochemistry* 30(37):9097–9101 (1991).

Matovcik, et al., "The recycling itinerary of the 46 kDa mannose 6–phosphate receptor—Golgi to late endosomes—coincides with that of the 215 kDa M6PR," *Eur. J. Cell. Biol.* 53(2):203–211 (1990).

(List continued on next page.)

*Primary Examiner*—David Guzo
*Assistant Examiner*—Jon Shuman
*Attorney, Agent, or Firm*—Arnall Golden & Gregory, LLP

[57] ABSTRACT

A method of detecting dysplastic regions within epithelial tissue samples is sensitive enough to detect and distinguish between low grade and high grade dysplastic regions. The method uses probes specific for expression and accumulation of substances within a particular intracellular region from a defect in apical membrane trafficking (trafficking markers) and in the preferred embodiment correlates the trafficking marker levels with the presence of an oncogene such as p53. If low grade dysplasia is present, trafficking markers are detected in a distinctive perinuclear pattern. Previous studies have demonstrated a high correlation of p53 over-expression with high grade dysplasia and adenocarcinoma. Detection of p53 is shown to be mutually exclusive of detection of trafficking markers. Therefore, dual detection for both the trafficking markers and p53 provides an accurate method for more precise grading of biopsies. This definitive assay and grading assists in identifying populations at risk for progression to adenocarcinoma. Preferred trafficking markers include Rab11, Rab25, g-adaptin and mannose-6-phosphate receptor.

15 Claims, No Drawings

OTHER PUBLICATIONS

Meltzer, et al., "Microsatellite Instability Occurs Frequently and in Both Diploid and Aneuploid Cell Populations of Barrett's–associated Esophageal Adenocarcinomas," *Cancer Res.* 54(13):3379–3382 (1994).

Miros, et al., "Only patients with dysplasia progress to adenocarcinoma in Barrett's oesophagus," *Gut* 32:1441–1446 (1991).

Nashat, et al., "p53 Mutations in Barrett's Adenocarcinoma and High–Grade Dysplasia," *Gastroenterology* 106(6):1589–1595 (1994).

Nishimaki, et al., "Histopathologic Characteristics of Early Adenocarcinoma in Barrett's Esophagus," *Cancer* 68(8):1731–1736 (1991).

Ovaska, et al., "Adenocarcinoma Arising in Barrett's Esophagus," *Dig. Dis. Sci.* 34(9):1336–1339 (1989).

Provenzale, et al., "A Guide for Surveillance of Patients with Barrett's Esophagus," *Am. J. Gastroenterol.* 89(5):670–680 (1994).

Raiha, et al., "Prevalence and Characteristics of Symptomatic Gastroesophageal Reflux Disease in the Elderly," *J. Am. Geriat. Soc.* 40(12):1209–1211 (1992).

Ray, et al., "Expression of RAB11, A Small GTP–binding Protein, In Dysplasia and Early Adenocarcinoma Arising in Barrett's Esophagus," *Gastroenterology* 110(4):A237 (1997).

Reid, et al., "Observer Variation in the Diagnosis of Dysplasia in Barrett's Esophagus," *Hum. Pathol.* 19(2):166–178 (1988).

Reid, et al., "Barrett's Esophagus—Correlation Between Flow Cytometry and Histology in Detection of Patients at Risk for Adenocarcinoma," *Gastroenterology* 93(1):1–11 (1987).

Reid, et al., "Endoscopic Biopsy Can Detect High–Grade Dysplasia or Early Adenocarcinoma in Barrett's Esophagus Without Grossly Recognizable Neoplastic Lesions," *Gastroenterology* 94(1):81–90 (1988).

Reid, et al., "Barrett's Esophagus and Esophageal Adenocarcinoma," *Gastroenterol. Clin. North Am.* 20(4):817–834 (1991).

Reid, et al., "Flow–Cytometric and Histological Progression to Malignancy in Barrett's Esophagus: Prospective Endoscopic Surveillance of a Cohort," *Gastroenterology* 102(4):1212–1219 (1992).

Riddell, et al. "Dysplasia in Inflammatory Bowel Disease: Standardized Classification with Provisional Clinical Applications," *J. Pathol.* 14(11):931–968 (1983).

Robertson, et al., "Value of endoscopic surveillance in the detection of neoplastic change in Barrett's oesophagus," *Br. J. Surg.* 75(8):760–763 (1988).

Robinson, et al., "Recruitment of Coat Proteins onto Golgi Membranes in Intact and Permeabilized Cells: Effects of Brefeldin A and G Protein Activators," *Cell* 69(1):129–138 (1992).

Sorsdahl, et al., "p53 and ras Gene Expression in Human Esophageal Cancer and Barrett's Epithelium: A Prospective Study," *Cancer Detect. Prevent.* 18(3):179–185 (1994).

Spechler, et al., "Medical Progress—Barrett's Esophagus," *New Eng. J. Med.* 315(6):362–371 (1986).

Starnes, et al., "Barrett's Esophagus—A Surgical Entity," *Arch. Surg.* 119(5):563–567 (1984).

Thompson, et al., "Barrett's Metaplasia and Adenocarcinoma of the Esophagus and Gastroesophageal Junction," *Hum. Pathol.* 14(1):42–61 (1983).

Ullrich, et al., "Rab11 Regulates Recycling through the Pericentriolar Recycling Endosome," *J. Cell Biol.* 135(4):913–924 (1996).

Urbe, et al., "Rab11, a small GTPase associated with both constitutive and regulated secretory pathways with PC12 cells," *FEBS Lett.* 334(2):175–182 (1993).

Vogelstein, et al., "Genetic Alterations During Colorectal–Tumor Development," *New Eng. J. Med.* 319(9):525–532 (1988).

Younes, et al., "p53 Protein Accumulation in Barrett's Metaplasia, Dysplasia, and Carcinoma: A Follow–up Study," *Gastroenterology* 105(6):1637–1642 (1993).

METHOD OF DETECTING AND GRADING DYSPLASIA IN EPITHELIAL TISSUE

U.S. GOVERNMENT RIGHTS

The U.S. Federal Government has rights in this invention by virtue of grant numbers DK48370 and DK43405 from the NIH NIDDK and a Veterans Administration Merit Award to James R. Goldenring.

FIELD OF THE INVENTION

This is in the area of the prevention and diagnosis of adenocarcinoma developed from dysplastic epithelial intermediation and more particularly in the field of an assay for the stages of dysplasia.

BACKGROUND OF THE INVENTION

Adenocarcinoma of the esophagus develops from metaplastic Barrett's columnar epithelia through the evolution of dysplastic epithelial intermediates. The role of dysplasia leading to adenocarcinoma is well established. Haggitt, R. C., Hum. Pathol. 25:982–993 (1994). A particularly strong relationship has been established between specialized intestinal-type Barrett's epithelium and adenocarcinoma (Haggitt, Hum. Pathol. 25:982–993 (1994); Hameeteman et al., Gastroenterology 96:1249–1256 (1989); Hamilton et al., Hum. Pathol. 19:942–948 (1988); Nishimaki et al., Cancer 68:1731–1736 (1991); Ovaska et al., Dig. Dis. Sci. 34:1336–1339 (1989); Reid et al., Gastroenterol. Clin. North Am. 20:817–834 (1991); Spechler et al., New Eng. J. Med. 315:362–371 (1986); Thompson et al., Hum. Pathol. 14:42–61 (1983)).

Gastroesophageal reflux disease is a common disorder affecting between 8 and 15% of the adult population in Western countries (Isolauri et al., Ann. Med. 27:67–70 (1995); Raiha et al., J. Am. Geriat. Soc. 40:1209–1211 (1992)). Columnar metaplasia of the esophagus, i.e. Barrett's esophagus, is reported in 8 to 24% of patients undergoing endoscopy for chronic symptomatic reflux (Haggitt, Hum. Pathol. 25:982–993 (1994); Ovaska et al., Dig. Dis. Sci. 34:1336–1339 (1989); Reid et al. Gastroenterol. Clin. North Am. 20:817–834 (1991); Spechler et al., New Eng. J. Med. 315:362–371 (1986)). Identification and follow-up of Barrett's esophagus is essential as these patients have a 30- to 40-fold increased risk of developing esophageal adenocarcinoma (Haggitt, Hum. Pathol. 25:982–993 (1994); Iftikhar et al., Gut 33:1155–1158 (1992); Reid et al., Gastroenterol. Clin. North Am. 20:817–834 (1991); Spechler et al., New Eng. J. Med. 315:362–371 (1986)).

Current management of Barrett's esophagus and specialized intestinal type Barrett's epithelium involves a program of endoscopic surveillance biopsies to detect dysplasia and early adenocarcinoma (Provenzale et al., Am. J. Gastroenterol. 89:670–680 (1994); Robertson et al., Br. J. Surg. 75:760–763 (1988)). High-grade dysplasia and early adenocarcinoma can be detected by endoscopic biopsy in patients without gross evidence of neoplasia (Levine et al., Gastroenterology 105:40–50 (1993); Reid et al., Gastroenterology 94:81–90 (1988)). While management of those patients with high-grade dysplasia remains controversial, the frequency of adenocarcinoma in the setting of advanced dysplasia (Haggitt, Hum. Pathol. 25:982–993 (1994); Miros et al., Gut 32:1441–1446 (1991); Starnes et al., Arch. Surg. 119:563–567 (1984)) has led to a recommendation for early resection.

Most authors agree that the development of adenocarcinoma in Barrett's esophagus, as well as other adenocarcinomas of the digestive tract, is preceded by a progression through increasing grades of dysplasia to carcinoma in situ and eventually to invasive cancer (Miros et al., Gut 32:1441–1446 (1991); Reid et al., Gastroenterology 102:1212–1219 (1992); Riddell et al. J. Pathol. 14:931–967 (1983)). These grades include non-dysplastic, low grade dysplasia, high grade dysplasia, carcinoma and eventually invasive cancer. Histological grading of dysplasia is subject to considerable variation among observers (Reid et al., Gastroenterology 93:1–11 (1987)). Consequently, many investigators have sought to characterize more objective changes in the dysplasia-adenocarcinoma sequence that would identify those patients with the greatest risk of developing cancer.

Recent studies suggest that mutations of the p53 tumor suppressor gene, as detected by immunohistochemistry or flow cytometry, may be predictive of progression to high-grade dysplasia and adenocarcinoma (Blount et al., Cancer Res. 51:5482–5486 (1991); Blount et al., Cancer Res. 54:2292–2295 (1994); Casson et al., Am. J. Surg. 167:52–57 (1994); Hardwick et al., Gut 35:764–768 (1994); Jones et al., Ann. Thorac. Surg. 57:598–603 (1994); Neshat et al., Gastroenterology 106:1589–1595 (1994); Sorsdahl et al., Cancer Detect. Prevent. 18:179–185 (1994); Younes et al., Gastroenterology 105:1637–1642 (1993)). Genetic instability, as determined by aneuploid or increased G2/tetraploid fractions in flow cytometric analysis, and cellular ultrastructural changes have been implicated in the development of adenocarcinoma (Levine et al., Gastroenterology 96:355–367 (1989); Meltzer et al., Cancer Res. 54:3379–3382 (1994); Reid et al., Gastroenterology 93:1–11 (1987); Reid et al., Gastroenterology 102:1212–1219 (1992)). Still, while the grading of high grade dysplasia has become more uniform, the reliable identification of low grade dysplasia versus readings of indeterminant or reactive changes remains problematic. Thus, no markers for low grade dysplasia have been identified. Furthermore, while a progression of dysplasia leading to adenocarcinoma is well accepted, little is known about the cellular changes occurring during the transition from Barrett's columnar epithelia to low grade dysplastic cells.

The grading of dysplastic cells in endoscopic biopsies remains the mainstay of prospective surveillance for patients with Barrett's esophagus. The frequency of endoscopic surveillance is strongly predicated on the determination of low or high grade dysplasia. The presence of high grade dysplasia or carcinoma in situ supports referral for early surgical resection. Evidence of low grade dysplasia has been suggested as an indication for greater vigilance in surveillance. Nevertheless, while grading of high grade dysplasia has relatively low interobserver variability, the grading of low grade dysplasia has been fraught with broad interobserver variability (Reid et al., Hum. Pathol. 19:166–178 (1988)).

The expression of a small GTP-binding protein, Rab11, has been recently described as an apically associated vesicle protein in a number of polarized epithelial tissues, including the gastric fundic, ileal, and colonic epithelia as well as the squamous epithelium of the esophagus (Goldenring et al., Am. J. Physiol. 270:G515–G525 (1996)). Rab11 was also expressed in a number of well-differentiated colonic adenocarcinoma cell lines (Goldenring et al., Am. J. Physiol. 270:G515–G525 (1996)). More recently, it has become apparent that Rab11 is a critical modulator of vesicle recycling to the plasma membrane (Calhoun et al., Yale J. Bio. Med. 69:1–8 (1996); Goldenring et al., Am. J. Physiol. 267:G187–G194 (1994); Green et al., Mol. Biol. Cell. 7:591

(1996); Ullrich et al., J. Cell Biol. 135:913–924 (1996); Urbe et al., FEBS Lett. 334:175–182 (1993)).

The evolution of adenocarcinoma appears to require a progression of cellular alterations through increasingly dysplastic lineages.

It is therefore an object of the present invention to provide a method and reagents to identify objective changes in the dysplasia-adenocarcinoma sequence that would identify patients with epithelium that have the greatest risk of developing cancer.

It is a further object of the present invention to provide methods and reagents for the reliable identification and grading of low grade dysplasia.

SUMMARY OF THE INVENTION

A method of detecting and grading dysplastic regions within epithelia is described. The method is sensitive enough to detect and distinguish between low grade and high grade dysplastic regions. The method uses probes specific for expression and distribution of markers which manifest changes in intracellular apical trafficking or vesicular recycling. The markers are detected by means known in the art, such as antibody staining and immuno-fluorescence. Preferred markers include substances that accumulate within an intracellular region when apical trafficking or vesicular recycling is blocked. Examples of such substances include Rab11 protein, Rab25 protein, g-adaptin protein and the mannose-6-phosphate receptor. In a preferred embodiment, the markers are correlated with the presence of an oncogene that mutually exclusively marks the presence of high grade dysplasia, such as p53.

As demonstrated in the examples, immunostaining of epithelial sections incubated with an antibody for one of the trafficking markers is predictive of dysplasia. If low grade dysplasia is present, a distinctive perinuclear immunostaining pattern is observed, thus providing a reliable standard for low grade dysplasia. Cells demonstrating perinuclear staining were found to be generally exclusive of those showing nuclear over-expression of p53 immunoreactive protein. Since previous studies have demonstrated a high correlation of p53 over-expression with high grade dysplasia, dual staining for both a trafficking marker and p53 provides an accurate method for more precise grading of epithelial sections and biopsies. This more definitive assay and grading assists in identifying populations at risk for progression to adenocarcinoma. The results presented here indicate that an increase in immunoreactivity of the trafficking markers coincides with the development of low grade dysplasia.

DETAILED DESCRIPTION OF THE INVENTION

A method of detecting and grading dysplasia in epithelial tissue is disclosed. Previous research has shown that p53 is expressed in tissue samples from an adenocarcinoma. The examples of the method show that trafficking markers are expressed in a distinctive perinuclear pattern in low grade dysplastic tissue and p53 is mutually exclusively expressed in the tumorous tissue. The method includes providing a tissue sample, incubating the tissue with probes for at least one trafficking marker and p53, and testing the tissue for reactions with the reagents, for example, by immunostaining of either marker. A distinctive perinuclear expression and accumulation pattern of a trafficking marker indicates low grade dysplasia and mutually exclusive nuclear staining of p53 indicates high grade dysplasia. Data presented and discussed are from photomicrographs of epithelial tissue.

Materials and Methods for Detecting Dysplasia

I. Materials and Reagents

A. Types of Tissues to be Tested

A method of marking and grading dysplastic regions within epithelia, especially epithelial tissue of the gastrointestinal tract and reproductive regions, such as the esophagus and cervix, as well epithelial tissue of the lung, breast, prostate and skin is described. Samples are obtained from patients suspected of being at risk of adenocarcinoma or during routine screening exams, especially of colon. Samples are obtained using standard methods for biopsy, resection and excisional biopsies, such as endoscopy.

Dysplasia is defined as abnormal development of tissue and is characterized by a loss of apical secretory specialization. Low grade dysplasia and high grade dysplasia are defined by criteria standard in the art, as described in Reid et al., Hum. Pathol. 19:166–178 (1988).

B. Trafficking Markers

Trafficking markers include substances that accumulate within a particular intracellular region from a defect in apical membrane trafficking, for example, when trafficking of post-Golgi vesicles is blocked, particularly those involved in recycling vesicles to the apical membrane. Examples of trafficking markers include Rab11 protein, Rab25 protein, g-adaptin protein and the mannose-6-phosphate receptor. The Rab11 protein and its sequence are described in Goldenring et al., Am. J. Physiol. 267:G187–G194 (1994). The Rab25 protein and its sequence are described in Calhoun et al., Biochem. J., 325:559–564 (1997).

Rab11 is present on the H/K-ATPase-containing tubulovesicles of gastric parietal cells (Calhoun et al., Biochem. J., 325:559–564 (1997); Goldenring et al., Am. J. Physiol. 267:G187–G194 (1994); Goldenring et al., Am. J. Physiol. 270:G515–G525 (1996)). Rab11 immunoreactivity was observed in a number of normal columnar epithelial cells in a subapical distribution (Goldenring et al., Am. J. Physiol. 270:G515–G525 (1996)). Urbe et al., have reported that Rab11 is present on both constitutive and regulated secretory vesicles of PC12 cells (Vogelstein et al., New Engl. J. Med. 319:525–532 (1988)). These studies have all supported a role for Rab11 in the trafficking of post-Golgi vesicles, particularly those involved in recycling to the apical membrane (Calhoun et al., Yale J. Bio. Med. 69:1–8 (1996)). Recent studies in transfected CHO cells (Ullrich et al., J. Cell Biol. 135:913–924 (1996)) and K562 cell (Green et al., Mol. Biol. Cell. 7:591 (1996)) indicate that Rab11 is present on the plasma membrane recycling system in non-polarized cells. In both PC12 cells and fibroblasts, a small amount of staining in the Golgi apparatus was also noted (Calhoun et al., Yale J. Bio. Med. 69:1–8 (1996); Ullrich et al., J. Cell Biol. 135:913–924 (1996)).

The disclosed method tests for expression and accumulation of the trafficking markers within an intracellular region. This is accomplished with techniques known in the field, for example, preparing labelled antibodies to the markers. Detection of the trafficking markers can also be made by screening for mRNA levels by preparing labelled oligonucleotides from sequences of the markers, or preparing primers for mRNA.

Monoclonal antibodies against Rab11 and Rab25 are described below. Monoclonal antibodies against g-adaptin can be purchased from Sigma Chemical Co., St. Louis, Mo. Polyclonal antibodies against the mannose-6-phosphate receptor are described in Matovcik et al., Eur. J. Cell. Biol. 53:203–211 (1990). Alternatively, secondary antibodies may be employed to detect the accumulation of the trafficking markers. This can be done, for example, by employing an alkaline phosphatase-conjugated secondary kit from Biogenex. Vector Red is a preferred chromogen choice. Other methods of detection include biotinylated-secondary/ streptavidin-conjugated horseradish peroxidase with 3-amino-9-ethylcarbazole (AEC) or 3,3'-diaminobenzidine (DAB) as chromagen substrates. Also, fluorescent secondary antibodies conjugated with different fluorochromes may be used. This methodology is especially appropriate for simultaneous staining of the sections with more than one antibody. Preferred secondaries can be purchased from Jackson Immunochemicals.

Additional means for detecting the probes include those that are known in the art, such as immunostains, radiolabels, fluorescence, enzymes, fluorochromes, chemiluminescence, and dyes. Examples of these detection methods include monoclonal antibodies that are directly conjugated with fluorescent dyes, alkaline phosphatase staining, horseradish peroxidase staining as described in Goldenring et al., Am. J. Physiol. 267:G187–G194 (1994) and fluorescence staining as described in Goldenring et al., Am. J. Physiol. 270:G515–G525 (1996).

c. Oncogenes

In a preferred embodiment the trafficking markers are correlated with the presence of an oncogene that mutually exclusively marks the presence of high grade dysplasia and/or adenocarcinoma in epithelial tissue, such as p53, a tumor suppressing gene.

It is known in the art that regions of high grade dysplasia demonstrate strong nuclear p53 staining. (Blount et al., Cancer Res. 51:5482–5486 (1991); Blount et al., Cancer Res. 54:2292–2295. (1994); Casson et al., Am. J. Surg. 167:52–57 (1994); Hardwick et al., Gut 35:764–768 (1994); Jones et al., Ann. Thorac. Surg. 57:598–603 (1994); Neshat et al., Gastroenterology 106:1589–1595 (1994); Sorsdahl et al., Cancer Detect. Prevent. 18:179–185 (1994); Younes et al., Gastroenterology 105:1637–1642 (1993)). However, the examples disclosed herein demonstrate that the p53 staining is mutually exclusive of the trafficking marker staining.

As with the trafficking markers, many types of markers and methods of detecting them are known in the field and can be used with this method. p53 antibodies are available from several vendors including Zymed, So. San Francisco, Calif., Novacastra, Newcastle-upon-Tyne, UK, and Sigma Chemical Corp., St. Louis, Mo.

II. Methods for Analyzing Tissue for Dysplasia

The method described is an assay for grading dysplastic tissue that historically has progressed to adenocarcinoma. Tissue samples to be tested are obtained via biopsies, resections and excisional biopsies. Tissues may be from a recent examination or from archival records. Expression and accumulation of trafficking markers are detected. Detection of the trafficking markers in a perinuclear pattern indicates low grade dysplasia. A perinuclear pattern is defined as being around a nucleus. The term supranuclear is used interchangeably herein. A lack of detection of the trafficking markers may indicate that the tissue is non-dysplastic, high grade dysplastic or adenocarcinomic. However, detection of expression of p53 used in conjunction with detection of accumulation of trafficking markers will provide additional information. Mutually exclusive p53 nuclear expression indicates high grade dysplasia or adenocarcinoma. Trafficking markers and oncogene markers may be detected on the same slide with a dual staining technique involving a two-color detection system.

The methods and reagents described herein will be further understood by reference to the following non-limiting examples.

The following materials and methods were used in the Examples.

I. Materials

New Zealand White rabbits were obtained from Shelton's Bunny Barn. Accudenz was purchased from Accurate Scientific (Westbury, N.Y.). $^{125}$1-labeled secondary immunoglobulin G (IgG) was from Du Pont-New England Nuclear (Boston, Mass.). All thermocycling reactions were performed in a PTC-100 programmable thermal controller (M.J. Research, Watertown, Mass.). Taq polymerase and fmol double-stranded sequencing kits were purchased from Promega (Madison, Wis.). Sequagel-6 sequencing gel was purchased from National Diagnostics. Oligonucleotide primers were synthesized by the Yale Department of Pathology DNA Synthesis Laboratory on an Applied Sciences model 380A synthesizer with subsequent cartridge purification.

Types of Tissue and Dysplasia

All tissue studies were performed retrospectively on archival material from formalin fixed tissues embedded in paraffin. In the examples presented and discussed, four esophageal specimens in multiple tissue blocks were examined from patients who had undergone esophageal resection for adenocarcinoma arising from Barrett's epithelia. One of the patients was resected at the Medical College of Georgia, while three were treated at the Emory University Clinics. Esophageal endoscopic biopsies from 60 patients with Barrett's epithelia were examined from patients treated at the Medical College of Georgia between 1992 and 1996.

Cervical tissue specimens were obtained from archival biopsies from the Medical College of Georgia.

Antibody Markers to Rabs, Oncogenes and Other Reagents

Monoclonal antibodies against Rab11 (8H10) and Rab25 (12C3) were prepared as peritoneal ascites fluid by the University of Georgia Monoclonal Facility and were used at a 1:400 dilution. Monoclonal antibodies against p53 were purchased from Zymed Corporation and were used undiluted. Monoclonal antibodies against g-adaptin were purchased from Sigma. Polyclonal antibodies against the mannose-6-phosphate receptor are described in Matovcik et al., Eur. J. Cell. Biol. 53:203–211 (1990). Polyclonal antibodies against Rab7 and Rab9 were obtained from Dr. Marino Zerial (EMBL, Heidelberg, Germany). Secondary alkaline phosphatase-conjugated avidin-biotin reagents were purchased from Biogenex, San Ramon, Calif. Vector Red alkaline phosphatase substrate was obtained from Vector Laboratories, Burlingame, Calif. All other reagents were of the highest quality available.

II. Methods

Construction of recombinant Rab11

The rab11 cDNA sequence from rabbit was cloned as previously described in Goldenring et al., Am. J. Physiol. 267:G187–G194 (1994). The rabbit Rab11 amino acid sequence is identical to that for humans. A full-length cDNA encoding rab11 was resolved by amplification of the rab11 sequence with specific sense and antisense primers (Rab11 sense, CATATGGGCACCCGCGACGACGA (SEQ ID No. 1); Rab11 antisense, CTAGATGTTCTGACAGCACTG (SEQ ID No. 2). The sense primer contained an Nde I restriction site on the extension of its 5' end. This sequence was cloned into Bluescript-T as described in Goldenring et al., Am. J. Physiol. 267:G187–G194 (1994). The authenticity of the cloned rab11 sequence and the clone orientation were confirmed by double-stranded sequencing. The rab11 sequence contains an Nde I sequence. Restriction digestion with Nde I and BamH I yielded two fragments, a 5' Nde I—Nde I fragment and a 3' Nde I-BamH I fragment. The Nde I—Nde I fragment and the Nde I-BamH I fragments were then sequentially ligated into pET19b (Novagen) previously cut with Nde I and BamH I. The resulting ligations were then transformed into HMS174, and the resulting colonies were screened for plasmids with the correct ligation orientation using the Rab11 sense and Rab11 antisense primers. The isolated rab11-pET19b plasmid was then transformed into BL21(DE3)pLysS for protein expression. Optimal protein expression was achieved by induction of an $OD_{600}=0.6$ culture with 1 mM isopropyl-β-D-thiogalactopyranoside and growth at 22° C. for 2 h. To harvest protein, bacteria from a 1-liter culture were pelleted at 2,000 g and then resuspended in lysis buffer containing 0.1% Triton X-100. The resuspended bacteria were then lysed by stirring for 30 min. at 4° C., followed by sonication. The lysate was cleared by centrifugation at 100,000 g, and the resulting supernate was chromatographed over nickel-affinity resin (His-Bind, Novagen). The recombinant Rab11 preparation eluted with imidazole was homogeneous as assessed by Coomassie blue staining of sodium dodecyl sulfate-polyacrylamide gel electrophoresis (SDS-PAGE)-resolved proteins. One liter of culture yielded 1–3 mg of recombinant protein.

Production Monoclonal Antibodies against Rab11 and Rab25

Recombinant Rab11 in complete Freunds adjuvant was injected subcutaneously and intraperitoneally with a primary inoculate of 100 μg followed subsequently with two boosting intraperitoneal immunizations of 50 μg in incomplete Freunds adjuvant. Titers were followed using enzyme-linked immunosorbent assay (ELISA) screening of recombinant protein adhered onto Immulon-2 microtiter plates. When serum titers reached greater than 1:100,000 the mice were boosted intraperitoneally with 25 μg of recombinant protein and then killed 3 days later. Spleens were removed, and splenocytes were isolated and fused according to the standard protocol of the University of Georgia Monoclonal Facility. Supernates of primary hybridoma colonies were screened by ELISA. Serial cloning by dilution was employed, and the final clones were evaluated for their utility in Western blots of recombinant Rab11, recombinant Rab25, and parietal cell homogenates.

Antibodies against Rab25 were produced as described in Calhoun et al., Biochem. J., 325:559–564 (1997), incorporated herein by reference. Because Rab25 and Rab11 are approximately 70% identical, obtaining a monoclonal antibody for Rab11 that did not cross react with Rab25 required special screening.

His-tagged recombinant rabbit Rab25 was prepared as previously described in Goldenring et al., J. Biol. Chem. 268:18419–18422 (1993), and purified by nickel-affinity (His-Bind) chromatography (Novagen, Madison, Wis., U.S.A.). Monoclonal antibody production was performed at the University of Georgia Monoclonal Antibody Facility as previously described in Goldenring et al., Am. J. Physiol. 270:G515–G525 (1996). Initial immunizations were performed with 150 μg of Rab25 with boost injections with 100 μg of protein. Hybridomas were screened by ELISA simultaneously for immunoreactivity against both recombinant Rab11 and Rab25. Only clones displaying selective immunoreactivity against Rab25 were propagated.

For competition studies, two synthetic peptides were constructed based on the C-terminal variable regions of Rab11. (QKQMSDRRENDMSPSNNVVPIHVPPTTENKPKVQ; SEQ. ID No. 3) and Rab25 (KVSKQIQNSPRSNAIALGSAQAGQEPGPGQKR; SEQ ID No. 4). In ELISA, the Rab11 peptide inhibited the binding of monoclonal antibody 8H10 to recombinant Rab11 with an $IC_{50}$ of 1 μg/ml. Similarly, the Rab25 C-terminal peptide inhibited the binding of 12C3 to recombinant Rab25 in ELISA with an $IC_{60}$ of 1 μg/ml. In Western blot competition assays, strips of either recombinant proteins (approx. 25 ng per strip) or gastric mucosal 100,000 g microsomes (approx. 25 μg per strip) were incubated overnight at room temperature with peptides and antibodies added together without preincubation.

Immunohistochemistry

Tissue blocks were obtained from the Medical College of Georgia Department of Anatomic Pathology and the Emory Clinic. Five mm sections were deparaffinized, rehydrated, and stained with hematoxylin and eosin. Replicate 5 mm sections were blocked with 1.5% normal goat serum in phosphate buffered saline (PBS) pH 7.4, then incubated with mouse monoclonal IgG antibodies against Rab11 (8H10 ascites; 1:400), human p53 (Zymed; prediluted), Rab25 (12C3 ascites; 1:300 or g-adaptin (1:100) for 2 hours at room temperature. The primary antibody was detected with an alkaline phosphatase anti-mouse IgG biotin-streptavidin detection kit (Biogenex). A red reaction product was developed with Vector Red alkaline phosphatase substrate (Vector Laboratories). The sections were counterstained with Mayer's hematoxylin and mounted. The slides were viewed with a Zeiss Axiophot microscope. For double labelling studies, sections were stained simultaneously with 8H10 monoclonal antibody and rabbit polyclonal anti-mannose-6-phosphate receptor (1:500) for 2 hours at room temperature, with secondary detection with simultaneous incubation with bodipy-labelled goat anti-mouse IgG and Cy3-labelled donkey anti-rabbit IgG. The double-labelled slides were viewed using confocal fluorescence microscopy (Molecular Dynamics, Sunnyvale, Calif.).

Coding of biopsies

Stained biopsy sections were examined by three blinded observers. Biopsy specimens were coded for dysplasia using standard criteria (Reid et al., Hum. Pathol. 19:166–178 (1988)). Rab11 immunostaining was considered positive if cells were labelled in a punctate perinuclear pattern. The results of the specimen grading were compared by analysis of variance with post hoc pairwise comparison of groups by the Newman-Keuls method.

EXAMPLE 1

Determining the Expression of Rab11 in Dysplastic Epithelial Tissue to Determine if Changes in Apical Trafficking are Present Since the development of dysplasia is characterized by the loss of apical secretory specializations, it was hypothesized that changes in apical trafficking might be involved in the dysplastic process. The expression of an important candidate regulator of apical trafficking, the small GTP binding protein, Rab11, in resection and biopsy tissue from patients with Barrett's esophagus was evaluated. Sections from esophageal resection specimens from four patients and endoscopic biopsies from 60 patients were stained with antibodies against Rab11 as well as Rab25 and protein markers of the Golgi apparatus and p53 protein.

The g-adaptin protein is a component of the AP-1 adapter complex responsible for budding of coated vesicles from the trans-Golgi stacks (Ahle et al., EMBO J. 7:919–929 (1988); Lindner et al., Biochemistry 30:9097–9101 (1991); Lindner et al., J. Biol. Chem. 267:16567–16573 (1992); Robinson et al., Cell 69:129–138 (1992)). The mannose-6-phosphate receptor also is present within the trans-Golgi cisternae and is associated with the recycling of proteins back to the Golgi cisternae (Klumperman et al. J. Cell. Biol. 121:997–1010 (1993); Matovcik et al., Eur. J. Cell. Biol. 53:203–211 (1990)).

Rab11 staining in low grade dysplastic regions was similar to that observed with monoclonal antibodies against Rab25 and g-adaptin and colocalized with staining for the Golgi marker, the mannose-6-phosphate receptor. In the esophageal adenocarcinoma resections, prominent Rab11 immunostaining was observed in the supranuclear region of low grade dysplastic cells. In contrast, regions of high grade dysplasia demonstrating strong nuclear p53 staining showed only diffuse or absent Rab11 staining. In endoscopic biopsies, 91% of biopsies read unanimously as low grade dysplasia, demonstrated supranuclear Rab11 staining. Fourteen percent of biopsies unanimously graded as without dysplasia demonstrated perinuclear Rab11 staining. No p53 immunostaining was observed in any of the low-grade dysplasia biopsy specimens. An increase in Rab11 immunoreactivity appears to correlate with low grade dysplasia, while p53 immunostaining correlates with high grade dysplasia. The co-localization of Rab11 staining with increased immunoreactivity for markers of the trans-Golgi system is consistent with a defect in apical trafficking due to an expansion of either the trans-Golgi compartment or the apical recycling vesicle system.

Atypia leading to adenocarcinoma of the cervix displays a similar pattern to that seen with Barrett's.

EXAMPLE 2

Determining the Expression of Rab11 in Metaplastic and Dysplastic Barrett's Epithelium of the Esophagus to Determine if Alterations in Intracellular Vesicle Membrane Processing are Present Given the phenotypic changes in cell morphology accompanying dysplastic conversion, it was hypothesized that the dysplastic process may involve alterations in intracellular vesicle membrane processing. Therefore, the expression of Rab11 in the metaplastic and dysplastic Barrett's epithelium of the esophagus was investigated. The results indicate that perinuclear immunostaining for Rab11 is associated with low grade dysplasia. This and the study described in Example 1 indicate that immunocytochemical assessment of both Rab11 and p53 may serve as an important measure for cellular changes involved in the dysplastic transition within Barrett's mucosa.

EXAMPLE 3

Comparison of Rab11 and p53 expression in Esophageal Adenocarcinoma Resections

Rab11 immunoreactivity was observed in a number of normal columnar epithelial cells in a subapical distribution (Goldenring et al., Am. J. Physiol. 270:G515–G525 (1996)). However, Rab11 immunoreactivity was not observed in non-dysplastic Barrett's epithelia.

Hemotoxylin and eosin ("H&E") staining for histological grading, Rab11 immunoreactivity, and p53 immunoreactivity in Barrett's mucosa adjacent to an esophageal adenocarcinoma from a single resection specimen were compared. Specimens were of specialized intestinal type Barrett's epithelium and divided into four groups: areas without dysplasia, areas of low grade dysplasia, areas of high grade dysplasia, and a poorly differentiated tumor. Each section was five µm.

Barrett's epithelia without dysplasia stained with H&E, but did not demonstrate staining with antibodies against either Rab11 or p53. Within the same sections, regions of low-grade dysplasia, which are characterized by loss of goblet cells, decreased intracellular mucin content, nuclear atypia, pseudostratification and hyperchromatism, were identified adjacent to the tumor. The corresponding low grade dysplastic regions showed numerous Rab11 immunoreactive cells in a well localized perinuclear staining pattern, but only scattered p53 staining cells. p53 immunostaining was observed generally only in cells that were Rab11 negative in adjacent sections, suggesting that cells over-expressing p53 did not display increased Rab11 staining.

Areas of high-grade dysplasia were also observed in the resection specimen. Corresponding cells in such regions demonstrated intense nuclear p53 immunostaining, but little Rab11 immunoreactivity. The histology of the tumor was consistent with a poorly differentiated adenocarcinoma. In corresponding tissue samples no Rab11 positive cells were seen within the invasive malignancy, however, numerous p53 immunoreactive cells were present within the tumor. The results are representative of all four esophageal resections examined.

EXAMPLE 4

Illustration of Supranuclear Localization of Rab11

Esophageal adenocarcinoma resections were employed to illustrate supranuclear localization of Rab11. The pattern of Rab11 immunoreactivity in low grade dysplastic cells was typically an intense perinuclear staining. In most cases, Rab11 immunostained, low grade dysplastic regions abutted non-staining grossly non-dysplastic Barrett's epithelium. Rab11 inmunoreactive cells were noted immediately adjacent to non-reactive specialized intestinal epithelium. In higher grade dysplastic cells, when staining was observed, the immunoreactivity was observed as a faint and diffuse punctate stain throughout the cells.

In biopsy specimens, a similar pattern of supranuclear staining also was observed in low grade dysplastic cells. In addition, several biopsies of non-dysplastic mucosal cells also demonstrated supranuclear staining.

EXAMPLE 5

Illustration of Co-Localization of Rab11 with other Vesicular Markers

Serial sections of tissue from esophageal resections were employed to illustrate co-localization of Rab11 immunoreactivity in low grade dysplastic cells with other vesicular markers. The supranuclear localization of Rab11 suggested that the accumulation of labelling might be localized to a perinuclear vesicular structure such as the Golgi apparatus or the apical membrane recycling system. Previous investigations have localized Rab11 to plasma membrane recycling vesicle systems (Calhoun et al., Biochem. J., 325:559–564 (1997); Goldenring et al., Am. J. Physiol. 270:G515–G525 (1996); Green et al., Mol. Biol. Cell. 7:591 (1996); Ullrich et al., J. Cell Biol. 135:913–924 (1996)). The association of a closely-related Rab protein, Rab25 (Goldenring et al., J. Biol. Chem. 268:18419–18422 (1993)), with Rab11-containing parietal cell tubulovesicles (Calhoun et al., Biochem. J., 325:559–564 (1997)) has been observed. Therefore, the distribution of Rab11 was compared with the distribution for Rab25, g-adaptin and mannose-6-phosphate receptor.

In the serial sections of tissue from esophageal resections, Rab25 immunoreactivity was observed in the same distribution as Rab11 in low grade dysplastic cells. Rab11 staining in low grade dysplastic cells was compared with an established marker of the trans-Golgi compartment, g-adaptin, a component of trans-Golgi coatamer complex. The pattern of g-adaptin staining was similar to that observed for Rab11. Dual immunofluorescence labelling studies were performed with monoclonal antibodies against Rab11 and polyclonal antibodies against the mannose-6-phosphate receptor, an important component of the trans-Golgi recycling system. Confocal immunofluorescence microscopy was used to observe the double labelled sections of Rab11 and the mannose-6-phosphate receptor. It was seen that the expanded perinuclear staining for each coincided with staining with antibodies against the other. Like Rab11, perinuclear staining for Rab25, g-adaptin and mannose-6-phosphate receptor was prominently increased in low grade dysplastic cells. Cells with higher grades of dysplasia or in frank tumor demonstrated decreased or absent staining with antibodies against Rab11, Rab25, the mannose-6-phosphate receptor and g-adaptin. No staining of the perinuclear structure was observed with antibodies against either Rab7 or Rab9, markers of the late endosomes. The accumulation of perinuclear immunoreactivity for Rab11, Rab25, and the Golgi markers, g-adaptin and mannose-6-phosphate receptor were observed in low grade dysplastic cells in all four resections.

The superposition of the Rab11 and mannose-6-phosphate receptor staining were superimposed. Using immunohistochemistry on serial sections, similar perinuclear staining for Rab11 and both Rab25 and g-adaptin was observed. In immunofluorescence double labelled sections observed in confocal microscopy, Rab11 and mannose-6-phosphate receptor staining colocalized in the perinuclear region of low grade dysplastic cells.

EXAMPLE 6

Determining Whether an Increase in Rab11 Immunoreactivity Indicates Low Grade Dysplasia and a Predisposition to Aneuploidy, p53 Mutation and Adenocarcinoma These studies of esophageal resections strongly suggest an association of Rab11 immunoreactivity with low grade dysplasia. Thus, it was sought to determine whether an increase in Rab11 immunoreactivity might be a useful marker for low grade dysplasia of Barrett's epithelium. Sixty specimens were obtained from archival tissue blocks of endoscopic esophageal biopsies of Barrett's patients obtained between 1992 and 1996. Thirty cases originally diagnosed as without dysplasia and 30 cases reported with low grade dysplasia were selected. These biopsies were stained with hematoxylin and eosin and for Rab11 immunoreactivity. Hematoxylin and eosin stains were coded blindly by three observers to establish dysplasia grading. Table I displays the pattern of staining according to dysplasia grade.

TABLE I

Grading of Dysplasia and Rab11 Staining in 60 Biopsies of Barrett's Epithelium.

|  | Number | Negative for Rab11 immunoreactivity | Positive for Rab11 immunoreactivity |
| --- | --- | --- | --- |
| No Dysplasia | 33 ± 1.5 | 24.3 ± 1.3* | 8.7 ± 1.7 |
| Low Grade Dysplasia | 27 ± 1.5 | 4.3 ± 0.9 | 22.7 ± 1.2* |

Data are shown ± SEM.
ANOVA was significant at $p < 0.001$.
*$p < 0.05$ by Neuman-Keuls compared with both the No dysplasia/Rab11 positive group and the Low grade dysplasia/Rab11 negative group.

No biopsies were graded as containing any regions of high grade dysplasia, neoplasia, adenocarcinoma or as being indeterminant. Eighty-four percent of low grade dysplastic mucosae stained for Rab11 with characteristic perinuclear immunoreactivity. Twenty-four percent of non-dysplastic biopsy samples displayed perinuclear staining. In general, staining in non-dysplastic cells was less intense than in low grade dysplastic regions, but did show a definite punctate perinuclear distribution. Notably, while there was considerable disagreement in conventional grading of biopsies as dysplastic or non-dysplastic, there was near unanimity in the grading of Rab11 staining. Thus, the three blinded observers graded from 25 to 30 biopsies as low grade dysplastic. The three observers disagreed on the grading of the histological samples in 10/60 or 17% of biopsies. This result is similar to that reported by Reid et al., Hum. Pathol. 19:166–178 (1988). However, all three observers agreed on the coding of Rab11 staining in 59/60 biopsies (98%). Thus, while there was disagreement over the number of dysplastic biopsies that were Rab11 negative, these disagreements were due to differences in histological grading. If the biopsies with discrepant histological grading are eliminated from the analysis, 91% of biopsies graded as low grade dysplasia demonstrated Rab11 staining, while 14% of non-dysplastic biopsies showed Rab11 immunoreactivity. Still, it is important to note that all three observers graded two of the biopsies as low grade dysplasia without observing Rab11 staining. The biopsy specimens also were stained for p53, however, no p53 immunoreactivity was observed in the nuclei of any low grade dysplastic biopsy samples.

The observation of an increase in Rab11 perinuclear immunostaining in low grade dysplastic cells could be explained by either an increase in expression or an accumulation of immunoreactive protein within a particular intracellular region.

An analysis of serial sections of dysplastic mucosa demonstrated similarities among the concentration of Rab11 immunostaining and labelling for both Rab25 and g-adaptin as well as the mannose-6-phosphate receptor. Thus, the colocalization of both Rab11 and Rab25 with the Golgi markers supports an alteration in apical plasma membrane trafficking at the level of the trans-Golgi leading to their accumulation along with the Golgi-markers. A previous electron microscopic examination of dysplastic mucosa in Barrett's epithelium suggested an expansion of the Golgi apparatus (Levine et al:, Lab. Invest. 60:418–431 (1989)). In that study, in low grade dysplastic cells, large perinuclear vacuolar structures were observed to contain electron-dense material. Importantly, the expanded vesicular structures were not observed in high-grade dysplastic or neoplastic cells. These results are similar to the loss of Rab11, Rab25 and Golgi marker staining that have been reported here in high-grade dysplastic and neoplastic cells. A diffuse punctate pattern for Rab11 staining in an esophageal adenocarcinoma cell line, SKGT-4 (Ray et al., Gastroenterology 110:A237 (1997)) has been observed. Thus, the transition from low grade dysplasia to high grade dysplasia/neoplasia may result in a resolution or bypassing of vesicle trafficking blockade commensurate with a more proliferative phenotype.

An alternate explanation also is possible. In recent studies, the presence of both Rab11 and Rab25 on immunoisolated parietal cell tubulovesicles was found (Calhoun et al., Biochem. J., 325:559–564 (1997)). It has also been observed that, in transfected MDCK cells, Rab11 and Rab25 localize to a subset of apical recycling vesicles. Thus, the localization of Rab11 and Rab25 within a defined membrane vesicle compartment is not without precedent. Given the data suggesting a role for Rab11 in recycling vesicle systems (Ullrich et al., J. Cell Biol. 135:913–924 (1996)), these observations could support an aberration in the recycling vesicle system in low grade dysplastic cells. A concentration of the putative recycling vesicle system has been noted in the presence of mutations in Rab11 that produce a constitutively active, GTPase-inactivated, form of the protein (Gray et al., Gastroenterology 103:1769–1776 (1992)). Therefore, the staining in dysplastic cells may represent a similar process of a dysfunctional recycling system. Long term dysfunction in the recycling system may lead to trapping of molecules for trafficking in and out of the trans-Golgi cisternae, such as g-adaptin and mannose-6-phosphate receptor, within the aberrant recycling system.

It is difficult to assess the absolute level of Rab11 expression in these serial sections of dysplastic mucosa specimens. Since the normal squamous epithelium expresses Rab11 at high levels, analysis of biopsy tissue for Rab11 protein or mRNA would not be informative. Similarly, analysis by in situ hybridization is hampered by the relatively low levels of mRNA expression and inconsistent preservation of mRNA in archival pathological specimens. Therefore, the disclosed Rab11 immunoassay is the most accurate method of marking and grading dysplasia.

Previous investigations have implicated aneuploidy and mutations in p53 protein in the development of high grade dysplasia. Vogelstein has stressed the linear progression of genomic changes during the progression from colonic adenoma to carcinoma. Staining for Rab11 immunoreactivity reveals a transition between benign and low grade dysplastic lineages, consistent with a genomic event leading to the evolution of the dysplastic cell (Vogelstein et al., New Engl. J. Med. 319:525–532 (1988)). The mutual exclusivity of perinuclear Rab11 staining and p53 overexpression suggests that the phenotype of the low-grade dysplastic lineage predisposes to the development of aneuploidy and p53 mutation.

Modification and variations of the methods and composition of the disclosed method and assay will be obvious to those skilled in the art from the foregoing detailed description. Such modifications and variations are intended to come within the scope of the following claims. For example, the disclosed method and assay are intended to include any kind of probe and means for detecting expression of trafficking markers, such as, Rab11, Rab25 and the Golgi markers. Expression of these trafficking markers is compared to any type of oncogene expression that mutually exclusively detects high grade dysplasia and adenocarcinoma.

We claim:

1. A method of detecting dysplasia in epithelial tissue samples comprising the steps:

providing probes for trafficking markers;

reacting the epithelial tissue samples with the probes; and detecting if the trafficking markers are present, wherein the trafficking markers are selected from the group consisting of Rab25 protein, g-adaptin protein and mannose-6-phosphate receptor and detection of the trafficking markers in a perinuclear pattern indicates low grade dysplasia and a risk of progression to adenocarcinoma.

2. The method of claim 1 wherein the perinuclear pattern of the trafficking markers further indicates aberrant membrane recycling.

3. The method of claim 1 wherein the perinuclear pattern of the trafficking markers further indicates aberrant vesicle trafficking.

4. The method of claim 1 wherein the trafficking marker is Rab25 protein.

5. The method of claim 1 wherein the epithelial tissue is Barrett's epithelia.

6. The method of claim 1 wherein the epithelial tissue is cervical or esophageal.

7. The method of claim 1 wherein the epithelial tissue is of the digestive tract, lung, or skin.

8. The method of claim 1 wherein the epithelial tissue is breast or prostate tissue.

9. The method of claim 1 wherein the probes are antibodies.

10. A method of detecting dysplasia in normal, non-dysplastic or pre-cancerous, low-grade dysplasia epithelial tissue samples comprising the steps:

providing probes for trafficking markers and for p53;

reacting the epithelial tissue samples with the probes for the trafficking markers and p53; and detecting if the trafficking markers and p53 are present, wherein the trafficking markers are selected from the group consisting of Rab11 protein, Rab25 protein, g-adaptin protein and mannose-6-phosphate receptor, and detection of the trafficking markers in a perinuclear pattern indicates low grade dysplasia and a risk of progression to adenocarcinoma, and mutually exclusive staining of the p53 without staining of the trafficking markers indicates high grade dysplasia and a risk of progression to adenocarcinoma.

11. The method of claim 10 wherein at least two serial sections are employed, a first serial section being incubated with antibodies against the trafficking markers and an adjacent serial section being incubated with antibodies against the p53.

12. The method of claim 10 wherein a single tissue section is dual stained with a two color detection system, one color for the p53 and one color for the trafficking markers.

13. The method of claim 10 wherein the perinuclear staining pattern of the trafficking markers or mutually exclusive staining for the p53 further indicates increased risk for developing aneuploidy and p53 mutations.

14. An antibody immunoreactive with a recombinant Rab25 protein that does not react with Rab11 protein.

15. An assay kit for testing for and grading dysplasia in epithelial tissue comprising an antibody to Rab25 protein.

\* \* \* \* \*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:1:

CATATGGGCA CCCGCGACGA CGA      23

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA

```
        (iii) HYPOTHETICAL: NO (iv) ANTI-SENSE: YES (xi) SEQUENCE DESCRIPTION: SEQ ID NO:2:

CTAGATGTTC TGACAGCACT G                                                         21

(2) INFORMATION FOR SEQ ID NO:3:

(i) SEQUENCE CHARACTERISTICS:
            (A) LENGTH: 34 amino acids
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:3:

Gln Lys Gln Met Ser Asp Arg Arg Glu Asn Asp Met Ser Pro Ser Asn
1               5                   10                  15

Asn Val Val Pro Ile His Val Pro Pro Thr Thr Glu Asn Lys Pro Lys
                20                  25                  30

Val Gln (2) INFORMATION FOR SEQ ID NO:4:

(i) SEQUENCE CHARACTERISTICS:
            (A) LENGTH: 32 amino acids
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:4:

Lys Val Ser Lys Gln Ile Gln Asn Ser Pro Arg Ser Asn Ala Ile Ala
1               5                   10                  15

Leu Gly Ser Ala Gln Ala Gly Gln Glu Pro Gly Pro Gly Gln Lys Arg
                20                  25                  30
```